United States Patent
Otani et al.

(10) Patent No.: US 11,549,940 B2
(45) Date of Patent: Jan. 10, 2023

(54) METHOD FOR DETECTING ANALYTE

(71) Applicant: Otsuka Pharmaceutical Co., Ltd., Tokyo (JP)

(72) Inventors: Makiko Otani, Tokyo (JP); Koji Miyazaki, Hino (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/641,880

(22) PCT Filed: Oct. 2, 2018

(86) PCT No.: PCT/JP2018/036777
§ 371 (c)(1),
(2) Date: Feb. 25, 2020

(87) PCT Pub. No.: WO2019/069885
PCT Pub. Date: Apr. 11, 2019

(65) Prior Publication Data
US 2020/0249226 A1 Aug. 6, 2020

(30) Foreign Application Priority Data
Oct. 2, 2017 (JP) .............................. JP2017-192684

(51) Int. Cl.
G01N 33/543 (2006.01)
G01N 33/68 (2006.01)

(52) U.S. Cl.
CPC ... G01N 33/54306 (2013.01); G01N 33/6887 (2013.01)

(58) Field of Classification Search
None
See application file for complete search history.

(56) References Cited

U.S. PATENT DOCUMENTS

| | | | | |
|---|---|---|---|---|
| 5,420,016 A | * | 5/1995 | Boguslaski et al. | C12Q 1/58 435/12 |
| 5,459,078 A | * | 10/1995 | Kline et al. | G01N 33/543 436/518 |
| 5,459,080 A | * | 10/1995 | Adamczyk | G01N 33/538 436/538 |
| 5,716,854 A | * | 2/1998 | Lofås | G01N 33/76 435/7.92 |
| 7,405,054 B1 | * | 7/2008 | Hasenbank | G01N 33/54373 436/514 |
| 2005/0249633 A1 | * | 11/2005 | Blatt | G01N 35/00009 422/400 |
| 2014/0193302 A1 | * | 7/2014 | Ookouchi | G01N 33/54393 422/69 |

FOREIGN PATENT DOCUMENTS

| | | | |
|---|---|---|---|
| EP | 2940473 | A1 | 11/2015 |
| JP | H06-508214 | A | 9/1994 |
| JP | H08-502586 | A | 3/1996 |
| JP | 2016-503294 | A | 2/2016 |
| JP | 2016-538827 | A | 12/2016 |
| WO | 92/021975 | A1 | 12/1992 |
| WO | 1992/021769 | A1 | 12/1992 |
| WO | 94/010573 | A1 | 5/1994 |
| WO | 1994/010573 | A1 | 5/1994 |
| WO | 2004/099253 | A1 | 11/2004 |
| WO | 2013/042603 | A1 | 3/2013 |
| WO | WO2013042603 | A1 | 3/2013 |
| WO | 2014/072306 | A1 | 5/2014 |
| WO | 2014/097877 | A1 | 6/2014 |
| WO | 2015/049355 | A1 | 4/2015 |
| WO | 2017/057136 | A1 | 4/2017 |

OTHER PUBLICATIONS

Kaya et al., English translation of WO 2013042603A1, Liquid for Diluting Specimen, Kit Using Same and Fluorometric Method using same, Patentscope translation, pp. 1-18. (Year: 2021).*

Zhang et al., Development of an Enzyme-linked Immunosorbet Assay for Seven Sulfonamide Residues and Investigation of Matrix Effect from Different Food Samples, J Agric. Food Chem. 2007, 55, pp. 2079-2084. (Year: 2007).*

Pearson et al., Surface plasmon resonance: a study of the effect of biotinylation on the selection of antibodies for use in immunoassay, Journal of Immunological Methods 221, 1998, pp. 87-94. (Year: 1998).*

Vancurova, Ivana, Cytokine Bioassay: Methods and Protocols, Methods in Molecular Biology, vol. 1172, 2014, Enhanced ELISA Based on Carboxymethylated Dextran Coatings, Chapter 4, pp. 39-47. (Year: 2014).*

International Search Report dated Dec. 11, 2018 for PCT/JP2018/036777 and English translation.

EPO, Extended European Search Report for the corresponding European patent application No. 18864747.3, dated Jun. 16, 2020.

"Reducing Non-Specific Binding," Life Sciences, Reichert Technologies, Surface Plasmon Resonance, Single Channel, Dual Channel and Modular System Platforms, Feb. 4, 2014.

EPO, Office Action for the corresponding European patent application No. 18864747.3, dated Mar. 12, 2021.

(Continued)

Primary Examiner — Gary Counts
(74) Attorney, Agent, or Firm — Lucas & Mercanti, LLP

(57) ABSTRACT

A method for detecting an analyte according to the present invention includes: a first step of supplying a specimen to a detection device having a first ligand that is immobilized on a substrate and is capable of specifically binding to the analyte, the specimen being supplied onto the substrate of the detection device, and then causing the analyte included in the specimen to bind to the first ligand; a second step of supplying, onto the substrate, a second ligand that is labeled with a marker and is capable of specifically binding to the analyte, and then causing the second ligand to bind to the analyte bound to the first ligand; and a third step of measuring the second ligand bound to the analyte, wherein in the second step, carboxymethyl dextran is supplied onto the substrate.

14 Claims, No Drawings

(56) References Cited

OTHER PUBLICATIONS

Takatoshi Kaya et al., Analytical Chemistry, vol. 87, No. 3, pp. 1797-1803, Feb. 3, 2015.
International Preliminary Report on Patentability dated Apr. 8, 2020 in the corresponding PCT application No. PCT/JP2018/036777.

* cited by examiner

METHOD FOR DETECTING ANALYTE

CROSS REFERENCE TO RELATED APPLICATION

This Application is a 371 of PCT/JP2018/036777 filed on Oct. 2, 2018, which, in turn, claimed the priority of Japanese Patent Application No. 2017-192684 filed on Oct. 2, 2017, both applications are incorporated herein by reference.

TECHNICAL FIELD

The present invention relates to a method for detecting an analyte, and more particularly, to a method for detecting an analyte by mainly using a biological sample as a specimen and detecting a trace amount of an analyte with high sensitivity.

BACKGROUND ART

In general immunoassays, an analyte (antigen) is bound to an immobilized first ligand (solid antibody), that analyte is bound to a labeled second ligand (labeled antibody), a sandwich system of first ligand-analyte-second ligand is formed, and at a time point when the binding of the first ligand, the analyte, and the second ligand has been achieved to a certain extent, the analyte is detected by measuring the labeled second ligand.

As one of such immunoassay devices, an SPFS device that enables detection of an analyte to be performed with high accuracy based on the principle of surface plasmon-field enhanced fluorescence spectroscopy (SPFS), to which a surface plasmon resonance phenomenon is applied, may be mentioned.

Surface plasmon-field enhanced fluorescence spectroscopy is a method for detecting an analyte in an infinitesimal amount at an ultralow concentration, by generating surface plasmon light (compressional waves) on a metal thin film surface under the conditions in which excitation light such as laser light irradiated from a light source undergoes attenuated total reflectance (ATR) at the metal thin film surface, thereby increasing the amount of photons carried by the excitation light irradiated from a light source to the range of from several dozen times to several hundred times, thus obtaining an effect of enhancing the electric field of the surface plasmon light, thereby efficiently exciting a fluorescent substance bound to an analyte captured in the vicinity of the metal thin film surface through this electric field enhancing effect, and observing this fluorescence.

An immunoassay such as SPFS is a highly sensitive method for detecting an analyte; however, in a case in which the binding force (affinity) between the analyte (antigen) and the second ligand (labeled antibody) is weak, since the second ligand cannot bind precisely to the analyte, the accuracy of detection for the analyte is not high.

As one method of enhancing the accuracy of detection for an analyte, a method of enhancing the accuracy of detection for an analyte by incorporating carboxymethyl dextran into a dilute solution of a specimen, thereby capturing the contaminants included in the specimen with carboxymethyl dextran, and thus suppressing an increase in the blank caused by the contaminants, is disclosed in Patent Literature 1.

However, in this method, an enhancement in the accuracy of detection brought by lowering of the blank can be expected; however, in a case in which the binding force between the analyte and the second ligand is weak, since the detection sensitivity for the analyte is not high per se, there are limitations in enhancing the accuracy of detection for the analyte.

CITATION LIST

Patent Literature

Patent Literature 1: WO 2013/042603

SUMMARY OF INVENTION

Technical Problem

An object of the present invention is to provide a method for detecting an analyte, in which in an immunoassay or the like, even in a case in which the binding force between an analyte as an object of measurement and a labeled ligand is weak, the detection sensitivity for the analyte is high.

Solution to Problem

The method for detecting an analyte according to the present invention, by which the object described above is achieved, includes:

a first step of supplying a specimen to a detection device having a first ligand that is immobilized on a substrate and is capable of specifically binding to the analyte, the specimen being supplied onto the substrate of the detection device, and then causing the analyte included in the specimen to bind to the first ligand;

a second step of supplying, onto the substrate, a second ligand that is labeled with a marker and is capable of specifically binding to the analyte, and then causing the second ligand to bind to the analyte bound to the first ligand; and a third step of measuring the second ligand bound to the analyte, wherein in the second step, carboxymethyl dextran is supplied onto the substrate.

With regard to the method for detecting an analyte, it is preferable that in the second step, carboxymethyl dextran is supplied onto the substrate at a concentration of 1 to 30 mg/mL.

With regard to the method for detecting an analyte, it is preferable that in the second step, carboxymethyl dextran is supplied onto the substrate together with the second ligand.

With regard to the method for detecting an analyte, it is preferable that in the second step, a second ligand-containing liquid containing the second ligand and carboxymethyl dextran is supplied onto the substrate.

With regard to the method for detecting an analyte, it is preferable that in the second step, the second ligand is supplied onto the substrate so as to cause the second ligand to bind to the analyte, and then carboxymethyl dextran is supplied thereonto.

With regard to the method for detecting an analyte, it is preferable that in the second step, after the second ligand is caused to bind to the analyte, carboxymethyl dextran is supplied by being incorporated into a cleaning liquid for cleaning the substrate.

With regard to the method for detecting an analyte, it is preferable that the analyte is cardiac troponin I (cTnI) or brain natriuretic peptide (BNP).

A kit for analyte detection of the present invention is a kit used for the method for detecting an analyte and includes a second ligand-containing liquid containing the second ligand and carboxymethyl dextran.

The kit for analyte detection of the present invention is a kit used for the method for detecting an analyte and includes a cleaning liquid for cleaning the substrate, the cleaning liquid containing carboxymethyl dextran.

Advantageous Effects of Invention

With the method for detecting an analyte of the present invention, even in a case in which the analyte is in a trace amount, and the binding force between the analyte and a labeled ligand is weak, the analyte can be detected with high sensitivity. The kit for analyte detection of the present invention can be used effectively for the method for detecting an analyte.

DESCRIPTION OF EMBODIMENTS

[Method for Detecting Analyte]

The method for detecting an analyte according to the present invention includes:

a first step of supplying a specimen to a detection device having a first ligand immobilized on a substrate and capable of specifically binding to the analyte, the specimen being supplied onto the substrate of the detection device, and then causing the analyte included in the specimen to bind to the first ligand;

a second step of supplying, onto the substrate, a second ligand labeled with a marker and capable of specifically binding to the analyte, and then causing the second ligand to bind to the analyte bound to the first ligand; and a third step of measuring the second ligand bound to the analyte, wherein in the second step, carboxymethyl dextran is supplied onto the substrate.

In general immunoassays, an analyte is indirectly detected by causing the analyte (antigen) to bind to a first ligand (solid antibody) immobilized on a substrate of a detection device in a first step; causing the analyte bound to the first ligand to specifically bind to a labeled second ligand (labeled antibody) in a second step; and measuring the labeled second ligand bound to the analyte by some kind of method in a third step. The method for detecting an analyte of the present invention has a feature of supplying carboxymethyl dextran onto the substrate in the second step described above.

In conventional immunoassays, in a case in which the binding force between an analyte and a labeled second ligand is weak, since the second ligand that serves as a target of measurement cannot bind precisely to the analyte, the analyte cannot be detected with high accuracy. According to the method for detecting an analyte according to the present invention, since carboxymethyl dextran is supplied onto the substrate in the second step, even in a case in which the binding force between the analyte and the labeled second ligand is weak, the analyte can be detected with high sensitivity. The reason why such an effect is obtained in the method for detecting an analyte according to the present invention is not clearly understood; however, it is speculated that since the carboxyl group of carboxymethyl dextran is hydrophilic, carboxymethyl dextran deprives the second ligand of the water of hydration, thereby the steric structure of the second ligand undergoes a change, the second ligand adopts a conformation that can react more easily with the analyte and thereby acquires higher reactivity with the analyte, the second ligand can bind precisely to the analyte, and thus the detection sensitivity for the analyte may be enhanced.

[First Step]

In the first step, a specimen is supplied to a detection device having a first ligand that is immobilized on a substrate and can specifically bind to an analyte, the specimen being supplied onto the substrate of the detection device, and then the analyte included in the specimen is caused to bind to the first ligand.

The detection device is, for example, a plasmon excitation sensor. The detection device has a substrate. As a suitable embodiment of the substrate in the case in which the detection device is a plasmon excitation sensor, the substrate has a support; a metal member formed on the support; a self-assembled monolayer (SAM) formed on the metal member; and a hydrophilic polymer layer formed on the SAM.

As the support, a transparent support is preferred because light irradiation of the metal member that will be described below is carried out through this support. Regarding the transparent support, the material is not particularly limited and may be a support made of glass or made of a plastic such as polycarbonate or a cycloolefin polymer. In the transparent support, the refractive index [nd] for the d-line (588 nm) is preferably 1.40 to 2.20, and the thickness is preferably 0.01 to 10 mm, and more preferably 0.5 to 5 mm.

Regarding a transparent support made of glass, commercially available products such as "BK7" (refractive index [nd] 1.52) and "LaSFN9" (refractive index [nd] 1.85) manufactured by Schott Japan Corp.; "K-PSFn3" (refractive index [nd] 1.84), "K-LaSFn17" (refractive index [nd] 1.88), and "K-LaSFn22" (refractive index [nd] 1.90) manufactured by Sumita Optical Glass, Inc.; and "S-LAL10" (refractive index [nd] 1.72) manufactured by Ohara Corp., are preferred from the viewpoints of optical characteristics and cleanability.

The metal member plays the role of generating surface plasmon or localized plasmon by means of light irradiated from a light source. Regarding the metal member, for example, a metal film or metal particles can be used, and it is preferable that the metal member is formed as a metal film on the surface of the support. This metal film plays the role of inducing surface plasmon by means of excitation light irradiated from a light source and efficiently exciting a fluorescent dye.

Regarding the metal for the metal film, it is preferable that the metal film is formed from at least one metal selected from the group consisting of gold, silver, copper, aluminum, platinum, and zinc, and it is more preferable that the metal film is formed from gold. The metal film may be in the form of being formed from an alloy of some of these metals, or may be a product obtained by laminating a plurality of metal films. Such a metal type is suitable from the viewpoint of being stable against oxidation and having large electric field enhancement caused by plasmon resonance.

In a case in which a support made of glass is used as the support, it is preferable that a thin film of chromium, a nickel-chromium alloy, or titanium is formed in advance on the support in order to adhere the glass and the metal film more firmly.

The thickness of the metal film is preferably 5 to 500 nm in the case of gold, 5 to 500 nm in the case of silver, 5 to 500 nm in the case of aluminum, 5 to 500 nm in the case of copper, 5 to 500 nm in the case of platinum, and 5 to 500 nm in the case of an alloy of those, and the thickness of a thin film of chromium is preferably 1 to 20 nm. From the viewpoint of electric field enhancement effect, the thickness of the metal film is more preferably 20 to 70 nm in the case of gold, 20 to 70 nm in the case of silver, 10 to 50 nm in the case of aluminum, 20 to 70 nm in the case of copper, 20 to 70 nm in the case of platinum, and 10 to 70 nm in the case of an alloy of those, and the thickness of a thin film of chromium is more preferably 1 to 3 nm. When the thickness of the metal film is within the range described above, it is suitable because surface plasmon is easily generated.

In the case of using metal particles as the metal member, it is possible to induce localized plasmon. The type of metal used for the metal particles is not particularly limited as long as particles capable of inducing plasmon can be produced therefrom; however, at least one metal selected from the group consisting of gold, silver, copper, aluminum, platinum, and zinc, or an alloy of two or more kinds of these is preferred. Furthermore, the particle size of the metal particles is not particularly limited as long as the particle size in the range capable of generating localized plasmon; however, the particle size is preferably 10 to 100 nm, and it is suitable to utilize clusters of metal particles having an average particle size in such a range.

For example, the metal particles can be used in the form of being dispersed on the above-mentioned support.

A Self-Assembled Monolayer (SAM) is formed on the other surface of the metal member, the surface not being in contact with the support, as a scaffold for solidifying the hydrophilic polymer layer that will be described below for the purpose of preventing metal quenching of fluorescent molecules at the time of fluorescence measurement.

Regarding the single molecules that form the SAM, usually, a carboxyalkanethiol having about 4 to 20 carbon atoms (can be purchased from, for example, Dojindo Molecular Technologies, Inc. or Sigma-Aldrich Japan K.K.), and particularly preferably 10-carboxy-1-decanethiol, is used. A carboxyalkanethiol having 4 to 20 carbon atoms is suitable from the viewpoint that the optical influence of a SAM formed using that compound is low, that is, the SAM has properties such as high transparency, a low refractive index, and a small film thickness.

The hydrophilic polymer layer is formed on the other surface of the SAM, the surface not being in contact with the metal member, and has a two-dimensional structure or a three-dimensional structure. A three-dimensional structure refers to a structure of the hydrophilic polymer layer, in which immobilization of the ligand that will be described below is not limited to the two-dimension of a support surface but is extended to a three-dimensional space separated from the support surface.

By using the hydrophilic polymer that will be described below in the form of a layer, the hydrophilic polymer layer can be used without being limited in the amount (concentration or density) of the hydrophilic polymer.

The polymer of the hydrophilic polymer layer refers to a compound having a molecular weight of 5,000 or more. Such a hydrophilic polymer may be at least one polymer selected from the group consisting of polysaccharide, polyethylene glycol, polyacrylic acid, and polymethacrylic acid. Polysaccharide is formed to include a structural unit derived from glucose and/or carboxymethylated glucose, and polyacrylic acid and polymethacrylic acid (these are also collectively referred to as "poly(meth)acrylic acid") is formed to include a structural unit derived from (meth)acrylic acid (that is, acrylic acid and methacrylic acid); however, these polymers can include a structural unit derived from the following monomer as appropriate. The monomer is preferably at least one selected from the group consisting of vinyl esters, acrylic acid esters, methacrylic acid esters, olefins, styrenes, crotonic acid esters, itaconic acid diesters, maleic acid diesters, fumaric acid diesters, allyl compounds, vinyl ethers, and vinyl ketones.

The polysaccharide is preferably a hydrophilic polymer such as dextran and/or a dextran derivative, and it is particularly suitable that the hydrophilic polymer layer is a hydrophilic polymer layer composed of dextran such as carboxymethyl dextran, from the viewpoint of enhancing biocompatibility, enhancing the suppressibility of a non-specific adsorption reaction, or securing high hydrophilicity.

The molecular weight of carboxymethyl dextran is preferably 1 kDa or more and 5,000 kDa or less, and more preferably 4 kDa or more and 1,000 kDa or less.

The density of the polymer of the hydrophilic polymer layer (mass per unit area of the hydrophilic polymer layer formed on the SAM) can be appropriately adjusted depending on the type of the polymer used or the layer forming method; however, for example, the density is 0.001 ng/mm$^2$ or more and 30 ng/mm$^2$ or less, and although the density may vary depending on the film thickness of the hydrophilic polymer layer, it is preferable that the density is in the range of 0.2 ng/mm$^2$ or more and 6 ng/mm$^2$ or less.

Particularly, in a hydrophilic polymer layer including dextran or a dextran derivative, preferably the density of the polymer satisfies this range. When a sensor chip in which a hydrophilic polymer is solidified at a density in such a range is used for the SAM, it is suitable because the assay luminescence signal is stabilized and increased.

The average film thickness of the hydrophilic polymer layer can be appropriately adjusted according to the type of the polymer used or the density of the layer. For example, the average film thickness may be 3 nm or more and 300 nm or less. Above all, the average film thickness is preferably 3 nm or more and 130 nm or less, and particularly preferably in the range of 50 nm or more and 100 nm or less. This film thickness can be measured using an atomic force microscope (AFM) or the like. When the average film thickness of the hydrophilic polymer layer is in such a range, it is suitable because the assay fluorescence signal is stabilized and increased. Meanwhile, the range of the average film thickness is the average film thickness in a solution such as an analyte solution that will be described below.

A first ligand is used for the purpose of immobilizing (capturing) an analyte in a specimen, and the first ligand is immobilized on the substrate, while according to a suitable embodiment of the substrate, the first ligand is immobilized on a hydrophilic polymer layer. In a case in which the hydrophilic polymer layer has a two-dimensional structure, the ligand is immobilized on the outer surface of the hydrophilic polymer layer, and in a case in which the hydrophilic polymer layer has a three-dimensional structure, the ligand is immobilized within the layer and/or on the outer surface of the hydrophilic polymer layer. In a case in which the hydrophilic polymer layer has a three-dimensional structure, generally, a large number of the ligands are immobilized in the form of being dispersed within the three-dimensional structure of the hydrophilic polymer layer.

The first ligand is a molecule or a molecule fragment, which can specifically recognize an analyte contained in a specimen or is specifically recognized by an analyte, and can bind to the analyte. Examples of such a molecule or molecule fragment include nucleic acids (DNA which may be single-stranded or double-stranded, RNA, a polynucleotide, an oligonucleotide, a PNA (peptide nucleic acid), and the like, or a nucleoside, a nucleotide, and modified molecules thereof), proteins (a polypeptide, an oligopeptide, and the like), amino acids (also including modified amino acids), saccharides (an oligosaccharide, a polysaccharide, a sugar chain, and the like), lipids, and modified molecules, complexes, and the like of these; however, the molecule or molecule fragment are not limited to these.

Examples of the proteins include antibodies, and specific examples include an anti-α-fetoprotein [AFP] monoclonal antibody (can be purchased from Japan Clinical Laboratories, Inc., and the like), an anticancer embryonal antigen [CEA] monoclonal antibody, an anti-CA19-9 monoclonal antibody, and an anti-PSA monoclonal antibody.

According to the present invention, the term "antibody" includes a polyclonal antibody or a monoclonal antibody, and an antibody obtainable by gene recombination, and an antibody fragment.

As a method for immobilizing a first ligand on a hydrophilic polymer layer, for example, a method of subjecting a carboxyl group carried by a polymer having a reactive functional group, such as carboxymethyl dextran [CMD], to active esterification by means of a water-soluble carbodiimide [WSC] (for example, 1-ethyl-3-(3-dimethylaminopropyl)carbodiimide hydrochloride [EDC]) and N-hydroxysuccinic acid imide [NHS], and immobilizing the carboxyl group that has been active esterified as such and an amino group carried by the first ligand by subjecting these groups to a dehydration reaction using a water-soluble carbodiimide, and the like may be mentioned.

After the first ligand is immobilized, it is preferable that the surface of the substrate is treated with a blocking agent such as bovine serum albumin [BSA], in order to prevent the specimen or the like that will be described below from non-specifically adsorbing to the substrate.

The density of the first ligand immobilized on the hydrophilic polymer layer is preferably 1 femtomol/cm$^2$ or more and 1 nanomol/cm$^2$ or less, and more preferably 10 femtomol/cm$^2$ or more and 100 picomol/cm$^2$ or less. When the density of the ligand is in the range described above, it is suitable because the signal intensity of the assay fluorescence signal becomes large.

The analyte is a substance that serves as an object of measurement and is usually included in a specimen. Examples of the specimen include blood (whole blood, blood serum and blood plasma), urine, nostril liquid, saliva, feces, and coelomic fluid (cerebrospinal fluid, ascites, pleural fluid, and the like). The specimen may be diluted as appropriate with a desired solvent, a desired buffer solution, or the like.

The analyte is a molecule or a molecule fragment that can be specifically recognized by the first ligand immobilized on the hydrophilic polymer layer or specifically recognize the first ligand and bind to the first ligand. Examples of the analyte include nucleic acids (DNA which may be single-stranded or double-stranded, RNA, a polynucleotide, an oligonucleotide, a peptide nucleic acid (PNA), and the like, and a nucleoside, a nucleotide, and modified molecules thereof), proteins (including a polypeptide and an oligopeptide), amino acids (also including modified amino acids), saccharides (an oligosaccharide, a polysaccharide, a sugar chain, and the like), lipids, and modified molecules, complexes, and the like of these. Specifically, the analyte may be cardiac troponin I (cTnI), brain natriuretic peptide (BNP), α-fetoprotein (AFP), a tumor marker such as a carcinoembryonic antigen, a signal transduction molecule, a hormone, or the like, and there are no particular limitations. Since it is speculated that the second ligand that will be described below has a steric structure which can easily react with the analyte, that is, a structure in which an antigen recognition site is exposed at the surface, the analyte is preferably cardiac troponin I (cTnI) or brain natriuretic peptide (BNP).

Since a specimen is usually supplied onto the substrate, the analyte binds to the first ligand that is immobilized on the substrate. It is preferable that a flow channel is formed on the substrate, and it is preferable that at least a portion of the flow channel is configured to include a metal member on a support and to include a hydrophilic polymer layer and a first ligand on a SAM, so that a specimen is delivered into the flow channel to immerse the first ligand in an analyte solution, and thereby the analyte is caused to bind to the first ligand.

The shape of the flow channel may be a square tube (pipe) or a round tube (pipe), it is preferable that the reaction unit and the measurement unit, in which the analyte is caused to bind to the first ligand or the like and fluorescence is measured, have a square tube shape, and it is preferable that the flow channel portion that is utilized only for the delivery of other chemical liquids or the like has a round tube shape.

Regarding the solvent used for diluting the specimen, for example, phosphate buffered saline [PBS], Tris buffered saline [TBS], and HEPES buffered saline [HBS] may be used.

In order to capture a large amount of the analyte using the first ligand, it is preferable that the delivered specimen is circulated in the flow channel. The temperature of the specimen and the time at that time may vary depending on the type of the specimen or the like; however, the temperature and time are usually 1 to 60 minutes at 20° C. to 40° C., and preferably 5 to 15 minutes at 37° C.

In a case in which the specimen is delivered to the flow channel, the initial concentration (concentration before delivery) of the analyte incorporated in the specimen is, for example, 0.001 pg/mL to 100 μg/mL. The total amount of the specimen to be delivered to the flow channel is usually 0.001 to 20 mL, and preferably 0.01 to 1 mL. The flow rate of the specimen to be delivered to the flow channel is usually 1 to 50,000 μL/min, and preferably 5,000 to 10,000 μL/min.

It is preferable that the specimen is supplied to the substrate, the analyte is caused to bind to the first ligand, and then the substrate is cleaned. Regarding the cleaning liquid to be used for cleaning, for example, a solution obtained by dissolving a surfactant such as Tween 20 or Triton X100 in the solvent used for dilution of the specimen, or another buffer solution (for example, PBS, TBS, or HBS) at a concentration of 0.00001% to 1% by mass, or a solution obtained by dissolving a salt such as sodium chloride or potassium chloride in the same solvent or buffer solution at a concentration of 10 to 500 mM, is preferred. Alternatively, a buffer solution having a low pH, for example, a 10 mM glycine hydrochloride buffer solution at pH 1.5 to 4.0, may also be used as the cleaning liquid.

It is preferable that the temperature and flow rate of the cleaning liquid are the same as the temperature and flow rate at the time of delivery of the specimen. Cleaning is usually carried out for 0.5 to 180 minutes, and preferably 5 to 60 minutes.

[Second Step]

In the second step, a second ligand that is labeled with a marker and can specifically bind to the analyte is supplied onto the substrate, and the analyte bound to the first ligand is caused to bind to the second ligand. Furthermore, in the second step, carboxymethyl dextran is supplied onto the substrate.

The second ligand is labeled with a marker and thus can specifically bind to the analyte. The second ligand is a ligand used for the purpose of performing labeling the analyte with a marker, and the second ligand may be the same as the first ligand as described above, or may be different therefrom. However, in a case in which the primary antibody used as the first ligand is a polyclonal antibody, the secondary antibody used as the second ligand may be a monoclonal antibody or a polyclonal antibody; however, in a case in which the primary antibody is a monoclonal antibody, it is desirable that the secondary antibody is a monoclonal antibody which recognizes an epitope that is not recognized by the primary antibody, or a polyclonal antibody.

Furthermore, an embodiment of using a complex in which a second analyte (competitive antigen; provided that this is different from the target antigen) that competes with the analyte (target antigen) included in the analyte solution has bound in advance to the secondary antibody, is also preferable. Such an embodiment is suitable because the amount of fluorescence (assay fluorescence signal) and the amount of the target antigen can be made proportional to each other.

The marker is a substance used for the purpose of detecting an analyte by causing a second ligand labeled with a marker to bind to the analyte and then measuring the marker by some kind of method, and as long as such a purpose is achieved, there are no limitations on the type of the marker. As the marker, a fluorescent dye is preferred, for the reason that high detection sensitivity is obtained, or the like. A fluorescent dye is a collective name for substances that emit fluorescent light when irradiated with predetermined excitation light, or when excited by utilizing an electric field effect. Fluorescence is a concept that also includes various kinds of luminescence such as phosphorescence.

Regarding the fluorescent dye, the type thereof is not particularly limited as long as the fluorescent dye is not completely quenched due to light absorption by the metal member, and any of known fluorescent dyes may be used. Generally, a fluorescent dye that enables a fluorescence system including a filter, rather than a monochromometer, to be used and has a large Stokes shift, which increases the efficiency of detection, is preferred.

Examples of such a fluorescent dye include fluorescent dyes of fluorescein family (manufactured by Integrated DNA Technologies, Inc.), fluorescent dyes of polyhalofluorescein family (manufactured by Applied Biosystems Japan, Ltd.), fluorescent dyes of hexachlorofluorescein family (manufactured by Applied Biosystems Japan, Ltd.), fluorescent dyes of coumarin family (manufactured by Invitrogen Corp.), fluorescent dyes of rhodamine family (manufactured by GE Healthcare Biosciences Corp.), fluorescent dyes of cyanine family, fluorescent dyes of indocarbocyanine family, fluorescent dyes of oxazine family, fluorescent dyes of thiazine family, fluorescent dyes of squaraine family, fluorescent dyes of chelated lanthanide family, fluorescent dyes of BODIPY (registered trademark) family (manufactured by Invitrogen Corp.), fluorescent dyes of naphthalenesulfonic acid family, fluorescent dyes of pyrene family, fluorescent dyes of triphenylmethane family, and Alexa Fluor (registered trademark) dye series (manufactured by Invitrogen Corp.), and furthermore, the fluorescent dyes described in U.S. Pat. Nos. 6,406,297, 6,221,604, 5,994,063, 5,808,044, 5,880,287, 5,556,959, and 5,135,717 can also be used.

Furthermore, the fluorescent dye is not limited to the organic fluorescent dyes described above. For example, fluorescent dyes of rare earth metal complex systems of Eu and Tb can also be used. Rare earth metal complexes generally have features of having a large wavelength difference between the excitation wavelength (about 310 to 340 nm) and the emission wavelength (near 615 nm for an Eu complex, and near 545 nm for a Tb complex), and having a long fluorescence lifetime of several hundred microseconds or more. An example of commercially available fluorescent dyes of rare earth metal complex systems may be ATBTA-$Eu^{3+}$.

When the fluorescence measurement that will be described below is carried out, it is desirable to use a fluorescent dye having the maximum fluorescence wavelength in a wavelength region with less light absorption by the metal included in the metal member. For example, in the case of using gold for the metal member, in order to suppress the influence exerted by light absorption by a gold member to a minimum level, it is desirable to use a fluorescent dye having a maximum fluorescence wavelength of 600 nm or longer. Therefore, in this case, it is particularly desirable to use a fluorescent dye having a maximum fluorescence wavelength in the near-infrared region, such as Cy5 or Alexa Fluor (registered trademark) 647. When such a fluorescent dye having a maximum fluorescence wavelength in the near-infrared region is used, it is useful also for the case of using blood as a specimen, from the viewpoint that the influence of light absorption by iron derived from a blood cell component in the blood can be suppressed to a minimum level. On the other hand, in the case of using silver as the metal member, it is desirable to use a fluorescent dye having a maximum fluorescence wavelength of 400 nm or more.

These fluorescent dyes may be used singly or in combination of two or more kinds thereof.

Regarding the method for producing a second ligand labeled with a marker, in the case of using a secondary antibody as the second ligand, examples include a method of first providing a fluorescent dye with a carboxyl group, subjecting the carboxyl group to active esterification by means of a water-soluble carbodiimide [WSC] (for example, 1-ethyl-3-(3-dimethylaminopropyl)carbodiimide hydrochloride [EDC]) and N-hydroxysuccinic acid imide [NHS], subsequently performing a dehydration reaction using the active esterified carboxyl group and an amino group carried by the secondary antibody, and thereby immobilizing the secondary antibody; a method of causing a secondary antibody and a fluorescent dye, respectively having an isothiocyanate group and an amino group, to react with each other and thereby immobilizing the secondary antibody; a method of causing a secondary antibody and a fluorescent dye, respectively having a sulfonyl halide group and an amino group, to react with each other and thereby immobilizing the secondary antibody; a method of causing a secondary antibody and a fluorescent dye, respectively having an iodoacetamide group and a thiol group, to react with each other and thereby immobilizing the secondary antibody; and a method of causing a biotinylated fluorescent dye and a streptavidinated secondary antibody (alternately, a streptavidinated fluorescent metal and biotinylated secondary antibody) to react with each other and thus immobilizing the secondary antibody.

When the second ligand labeled with a marker is supplied onto a substrate of a detection device, a solution including the second ligand labeled with a marker can be delivered onto the substrate of the detection device, and the concentration of the second ligand labeled with a marker in the solution to be delivered is preferably 0.001 to 10,000 µg/mL, and more preferably 1 to 1,000 µg/mL.

When this solution is delivered, the temperature, flow rate, and delivery time for the solution are respectively similar to those in the case of delivery of the specimen in the first step.

It is preferable that the second ligand labeled with a marker is supplied onto the substrate, the second ligand labeled with a marker is caused to bind to the analyte bound to the first ligand, and then the substrate is cleaned. This cleaning is similar to the cleaning in the first step.

In the second step, as described above, carboxymethyl dextran is supplied onto the substrate. Regarding the embodiment of supplying carboxymethyl dextran, specifically, an embodiment of supplying carboxymethyl dextran together with the second ligand, and an embodiment of supplying the second ligand onto the substrate, causing the second ligand to bind to the analyte, and then supplying carboxymethyl dextran, may be mentioned. In the case of the former embodiment, it is speculated that carboxymethyl dextran deprives the second ligand dissolved in the specimen of the water of hydration, thereby the steric structure of the second ligand undergoes a change, the second ligand adopts a conformation that may react more easily with the analyte to thereby acquire higher reactivity with the analyte, and thus the detection sensitivity for the analyte is enhanced. In the case of the latter embodiment, it is speculated that carboxymethyl dextran deprives the second ligand bound to the analyte of the water of hydration, the second ligand is changed to have a conformation having high affinity with the analyte, and dissociation of the analyte and the second ligand is suppressed, and thereby the detection sensitivity for the analyte is enhanced.

Regarding an embodiment of supplying carboxymethyl dextran together with the second ligand, a method of supplying a second ligand-containing liquid that contains the second ligand and carboxymethyl dextran may be mentioned. Regarding an embodiment of supplying the second ligand onto the substrate, causing the second ligand to bind to the analyte, and then supplying carboxymethyl dextran, a method of causing the second ligand to bind to the analyte, and then supplying carboxymethyl dextran in the form of being incorporated in a cleaning liquid for cleaning the substrate, may be mentioned.

The concentration of the carboxymethyl dextran to be supplied is preferably 1 to 30 mg/mL, and more preferably 1 to 10 mg/mL. When the concentration of the carboxymethyl dextran is in the above-described range, high detection sensitivity for the analyte may be easily obtained. Furthermore, when the concentration of the carboxymethyl dextran is more than 30 mg/mL, it is difficult to dissolve carboxymethyl dextran, the viscosity becomes high, and the operation may be achieved with difficulties.

The molecular weight of carboxymethyl dextran is preferably 10,000 to 1,000,000, more preferably 40,000 to 750,000, and even more preferably 100,000 to 500,000. When the molecular weight of carboxymethyl dextran is in the above-described range, high detection sensitivity for the analyte may be easily obtained.

The degree of substitution of the carboxyl groups of carboxymethyl dextran is preferably 0.2 to 0.8, and more preferably 0.4 to 0.7. When the degree of substitution of the carboxyl groups of carboxymethyl dextran is in the above-described range, high detection sensitivity for the analyte may be easily obtained. Meanwhile, the degree of substitution of the carboxyl groups of carboxymethyl dextran is defined as the proportion in which residues have been substituted with carboxyl groups in one molecule of carboxymethyl dextran.

[Third Step]

In the third step, the second ligand bound to the analyte is measured. The method for measuring the second ligand is determined as appropriate according to the types of the marker for labeling the second ligand and the detection device.

In a case in which the detection device is a plasmon excitation sensor described in the first step, and the marker is a fluorescent dye, the third step can be carried out as follows.

The sensor chip of the plasmon excitation sensor is irradiated with laser light via a prism through a surface of the support, the surface having no metal member formed thereon, the amount of fluorescence emitted from the excited fluorescent dye is measured, and the amount of the analyte included in the specimen is calculated from the measurement results.

The light source for irradiation at the time of measuring the amount of fluorescence is not particularly limited as long as the light source is capable of inducing plasmon excitation; however, from the viewpoints of the unity of the wavelength distribution and the power of light energy, it is preferable to use laser light as the light source. Regarding the laser light, it is desirable to regulate the energy and the amount of photons immediately before the light enters the prism, through an optical filter.

Surface plasmon is generated on the surface of the metal member by irradiation of laser light under attenuated total reflectance conditions [ATR]. As a result of an electric field enhancement effect of the surface plasmon, the fluorescent dye is excited by photons, the quantity of which has increased to several dozen to several hundred times the amount of irradiated photons. Meanwhile, the amount of photons increased by the electric field enhancement effect is dependent on the refractive index of the support, and the metal type and the film thickness of the metal member; however, the amount of increase is usually about 10 to 20 times in the case of gold.

In a fluorescent dye, when electron in the molecules is excited by light absorption and moves to a first electron excitation state in a short time period, and the electron returns from this state (level) to the ground state, the fluorescent dye emits fluorescence at the wavelength corresponding to the energy difference.

The type of the light source is not particularly limited, and the light source may not be a laser diode. Examples of the light source include a light emitting diode, a mercury lamp, and other laser light sources. In a case in which the light emitted from the light source is not a beam, the light emitted from the light source is converted to a beam by means of a lens, a mirror, a slit, or the like. Furthermore, in a case in which the light emitted from the light source is not monochromatic light, the light emitted from the light source is converted to monochromatic light by means of a diffraction grating or the like. Furthermore, in a case in which the light emitted from the light source is not linearly polarized light, the light emitted from the light source is converted to linearly polarized light by means of a polarizer or the like.

The prism is intended to allow laser light that has passed through various filters such as an optical filter, a polarizing filter, and a cutoff filter, which are used as necessary, to efficiently enter the metal member, and thus it is preferable that the refractive index is the same as that of the transparent support. In the present invention, various prisms with which the total reflection conditions can be set can be selected as appropriate, there are no particular limitations on the angle and shape, and for example, the prism may be a 60-degree dispersion prism. Examples of commercially available products of such a prism include those similar to the commercially available products of the transparent support made of glass as described above.

Examples of the optical filter include a dimming [ND] filter and a diaphragm filter. A dimming [ND] filter (or neutral density filter) is intended to regulate the amount of incident laser light. Particularly, in the case of using a detector having a narrow dynamic range, it is preferable to use a dimming filter from the viewpoint of performing measurement with high accuracy.

A polarizing filter is used to convert laser light into P-polarized light that efficiently generates surface plasmon.

A cutoff filter is a filter that removes optical noises such as light from the outside (illumination light outside an apparatus), excitation light (transmitted component of excitation light), stray light (scattered component of excitation light at various sites), and scattered light of plasmon (scattered light originating from excitation light and generated under the effect of structures, attachments, or the like on the sensor chip surface), and autofluorescence of fluorescent dyes, and examples include an interference filter and a color filter.

A condenser lens is used for the purpose of efficiently condensing fluorescence signals into a detector for measuring the amount of fluorescence, and any arbitrary condenser lens may be used. As a simple condenser lens, commercially available objective lenses (for example, products manufactured by Nikon Corp. or manufactured by Olympus Corp.) that are used in microscopes and the like may be diverted. The magnification ratio of the objective lens is preferably 10 to 100 times.

The detector is preferably a photomultiplier tube (photomultiplier manufactured by Hamamatsu Photonics K.K.), from the viewpoint of ultrahigh sensitivity. Furthermore, a CCD image sensor capable of multipoint measurement is also suitable, since although the sensitivity is lower compared to those devices, images can be viewed, and it is easy to eliminate noise light.

Regarding the method for calculating the amount of an analyte included in a specimen from measurement results, specifically, a method of producing a calibration curve by performing measurement of a target antigen or target antibody at a known concentration, and calculating the amount of the analyte (target antigen) in the specimen from the measurement signal on the basis of the calibration curve, may be mentioned.

Furthermore, by using the blank luminescence signal measured before the second step, the assay luminescence signal obtained in the third step, and the initial noise signals obtained by immobilizing a metal substrate that is not modified with anything in the flow channel and making measurement while causing ultrapure water to flow therethrough, the S/N ratio represented by the following Formula (Ia) can be calculated:

$$S/N = |Ia/Io|/In \quad (Ia)$$

wherein in the Formula (Ia), Ia represents the assay luminescence signal; Io represents the blank emission signal; and In represents the initial noise signal.

However, on the occasion of calculating the S/N, for practical use, the ratio may be calculated according to the following Formula (Ib), instead of the Formula (Ia), based on the assay noise signal obtainable in the case in which the concentration of the analyte included in the specimen is 0:

$$S/N = |Ia|/|Ian| \quad (Ib)$$

wherein in the Formula (Ib), Ian represents the assay noise signal; and Ia represents the assay luminescence signal similar to the case of the Formula (Ia).

[Kit for Analyte Detection]

A kit for analyte detection according to the present invention is a kit used for the method for detecting an analyte as described above, and includes a second ligand-containing liquid containing a second ligand and carboxymethyl dextran, or a cleaning liquid for cleaning the substrate, the cleaning liquid containing carboxymethyl dextran.

It is preferable that the kit for analyte detection includes all constituents that are necessary except for the specimen, upon performing the method for detecting an analyte. In a case in which the detection device is a plasmon excitation sensor described in connection with the first step, it is preferable that the kit for analyte detection includes at least a sensor chip (having at least a metal member, a SAM, a hydrophilic polymer layer, and a ligand on a support), and a second ligand-containing liquid containing a second ligand and carboxymethyl dextran, or a cleaning liquid for cleaning the substrate, the cleaning liquid containing carboxymethyl dextran. A more preferred kit for analyte detection includes all necessary constituents except for a specimen and ligands upon performing the assay method of the present invention. In a case in which the detection device is a plasmon excitation sensor described in connection with the first step, the kit for analyte detection includes at least a sensor chip having no ligand immobilized thereon (at least a metal member, a SAM, and a hydrophilic polymer on a support), and a second ligand-containing liquid containing a second ligand and carboxymethyl dextran, or carboxymethyl dextran. In the case of using such a kit for analyte detection, since a desired ligand (for example, a specific antibody) can be easily immobilized on the hydrophilic polymer layer carried by the sensor chip, the general-purpose usability of the kit of the present invention is further enhanced.

By using such a kit for analyte detection together with, for example, blood or blood serum as a specimen and an antibody to a specific tumor marker, the content of a specific tumor marker can be detected with high sensitivity and high accuracy. From these results, the existence of non-infiltrating carcinoma (intraepithelial carcinoma) of a pre symptomatic phase, which cannot be detected by palpation or the like, can also be predicted with high accuracy.

EXAMPLES (1) Production of Detection Device

A transparent support made of glass ("S-LAL 10" manufactured by Ohara Corp.) having a refractive index [nd] of 1.72 and a thickness of 1 mm was cleaned with plasma, a chromium thin film was formed by a sputtering method on one surface of the support, and then on that surface, a gold thin film as a metal member was formed over the transparent support by a sputtering method. The thickness of the chromium thin film was 1 to 3 nm, and the thickness of the gold thin film was 42 to 47 nm.

The support having a gold thin film formed as such was immersed for 24 hours in 10 mL of an ethanol solution of 10-amino-1-decanethiol prepared at 1 mM, and thus a SAM was formed on one surface of the gold thin film. Subsequently, this support was taken out from the ethanol solution and was cleaned respectively with ethanol and isopropanol, and then the support was dried using an air gun.

Subsequently, the support having a SAM formed thereon was immersed for one hour in a IVIES buffered saline [MES] (ionic strength 10 mM) at pH 7.4 including 1 mg/mL of a carboxymethyl dextran [CMD] having a molecular weight of 500,000, N-hydroxysuccinic acid imide [NHS] at 0.5 mM, and a water-soluble carbodiimide [WSC] at 1 mM, thus CMD was immobilized as a hydrophilic polymer layer on the SAM, and unreacted succinic acid ester was hydrolyzed by immersing the support for 30 minutes in a 1 mol/liter aqueous solution of NaOH. The average film thickness of the CMD layer was 70 nm, and the density was 5.0 ng/mm$^2$.

Subsequently, the support was immersed for one hour in MES including NHS at 50 mM and WSC at 100 mM and then was immersed for 30 minutes in an anti-human troponin I IgG monoclonal antibody "antibody" solution (Hytest, Ltd.) solution, and thereby a primary antibody was immobilized as a first ligand to CMD.

Furthermore, the support was subjected to a non-specific adsorption preventing treatment by circulating and delivering for 30 minutes PBS including 1 mass % bovine serum albumin [BSA] and 1 M aminoethanol.

A detection device was produced by mounting a flow channel member on the support having the primary antibody immobilized thereon. The flow channel member has flow channel a and flow channel b reaching from the upper surface to the lower surface of the flow channel member and has a concavity in the lower surface part, and the flow channel member has a structure in which the lower ends of the flow channel a and the flow channel b respectively lead to the two ends of the concavity. By mounting this flow channel member on the support, the concavity is covered by the support as a lid, and thereby a reaction chamber (measurement region) is formed. The immobilized primary antibody is accommodated in this reaction chamber. That is, the detection device has flow channel a and flow channel b reaching from the upper surface of the flow channel member to the upper surface of the support; and a reaction chamber that leads to the flow channel a and the flow channel b at the two ends and accommodates a primary antibody. In the detection device, a liquid is injected into the flow channel a and is sent to the reaction chamber, and then the liquid can be discharged through the flow channel b.

(2) Production of Ligand Labeled with Marker

An Alexa Fluor 647-labeled antibody was produced using an anti-human troponin I IgG monoclonal antibody "antibody" solution (Hytest, Ltd.) and an Alexa Fluor 647 labeling kit (Invitrogen Corp.), according to the predetermined procedure of the kit. Subsequently, unreacted reactants were removed using a molecular weight cutoff filter (Nihon Millipore K.K.), the Alexa Fluor 647-labeled antibody was purified, and the antibody was stored at 4° C. until the following assay was carried out.

Example 1

(First Step)

0.1 mL of a PBS solution including human troponin I at 100 pg/mL (0.1 ng/mL) was delivered to the reaction chamber through the flow channel a of the detection device. Subsequently, Tris buffered saline (TBS) including 0.05% by mass of Tween 20 was delivered to the reaction chamber through the flow channel a, to the flow channel of a detection device for SPFS, and was circulated for 10 minutes, and thus the flow channel and the reaction chamber were cleaned.

(Second Step)

A PBS solution including the Alexa Fluor 647-labeled antibody at a concentration of 2 μg/mL and carboxymethyl dextran (trade name CMD-500, manufactured by Meito Sangyo Co., Ltd., molecular weight: 500,000) at a concentration of 2.5 mg/mL was delivered to the reaction chamber through the flow channel a of the detection device. Subsequently, Tris buffered saline (TBS) including 0.05% by mass of Tween 20 was delivered to the reaction chamber through the flow channel a and was circulated for 10 minutes, and thus the flow channel and the reaction chamber were cleaned.

(Third Step)

The flow channels were brought to a state of being filled with PBS buffer (pH 7.4), subsequently the rear surface of the metal thin film of the measurement region was irradiated with laser light (640 nm, 40 μW) via a prism (manufactured by Sigma Koki Co., Ltd.), and the amount of fluorescence was measured using a photomultiplier tube (PMT) installed over the measurement region. This measurement value was designated as the assay luminescence signal Ia at a troponin I concentration of 100 pg/mL.

On the other hand, a PBS solution that did not include troponin I at all (0 pg/mL) was delivered, instead of the PBS solution including 100 pg/mL of troponin I, and the amount of fluorescence was measured by a procedure similar to that described above, except for that. This measurement value was designated as assay noise signal Ian.

The S/N ratio was determined according to the above Formula (Ib). The values of Ia, Ian, and S/N ratio thus obtained are presented in Tables 1 and 2. Furthermore, the ratio of the increased S/N ratio with respect to the S/N ratio obtained in the following Comparative Example 1 is presented in Table 2 as the increase rate of S/N ratio.

Meanwhile, the carboxymethyl dextran used in the second step in each Example is described as "CMD" as an "Additive substance" in Tables 1 and 2.

Examples 2 to 4

In Examples 2 to 4, detection of the analyte was carried out in the same manner as in Example 1, except that in the second step described above, the concentration of carboxymethyl dextran in the PBS solution including the Alexa Fluor 647-labeled antibody and carboxymethyl dextran was changed to 5 mg/mL, 10 mg/mL, and 30 mg/mL, respectively. The values of Ia, Ian, and S/N ratio thus obtained are presented in Table 1.

Comparative Example 1

Detection of the analyte was carried out in the same manner as in Example 1, except that in the second step, a PBS solution that included the Alexa Fluor 647-labeled antibody at a concentration of 2 μg/mL but did not include carboxymethyl dextran was used in place of the PBS solution including the Alexa Fluor 647-labeled antibody at a concentration of 2 μg/mL and carboxymethyl dextran at a concentration of 2.5 mg/mL. The values of Ia, Ian, and S/N ratio thus obtained are presented in Tables 1 and 2.

Comparative Example 2

Detection of the analyte was carried out in the same manner as in Example 1, except that in the second step, a PBS solution including the Alexa Fluor 647-labeled antibody at a concentration of 2 μg/mL and 1% by mass of polyethylene glycol (PEG #4000, manufactured by Wako Pure Chemical Industries, Ltd.) was used in place of the PBS solution including the Alexa Fluor 647-labeled antibody at a concentration of 2 μg/mL and carboxymethyl dextran at a concentration of 2.5 mg/mL. The values of Ia, Ian, and S/N ratio thus obtained are presented in Table 1.

Meanwhile, the polyethylene glycol used in the second step in Comparative Examples 2 to 4 is described as "PEG" as an "Additive substance" in Table 1.

Comparative Examples 3 to 4

In Comparative Examples 3 and 4, detection of the analyte was carried out in the same manner as in Comparative Example 2, except that in the second step, the concentration of polyethylene glycol in the PBS solution including the Alexa Fluor 647-labeled antibody and polyethylene glycol was changed to 3% by mass and 5% by mass, respectively. The values of Ia, Ian, and S/N ratio thus obtained are presented in Table 1.

Examples 5 to 9

In Examples 5 to 9, detection of the analyte was carried out in the same manner as in Example 1, except that the carboxymethyl dextran used in the second step was changed to carboxymethyl dextran (manufactured by Meito Sangyo Co., Ltd., molecular weight: 10,000), carboxymethyl dextran (manufactured by Meito Sangyo Co., Ltd., molecular weight: 40,000), carboxymethyl dextran (manufactured by Meito Sangyo Co., Ltd., molecular weight: 200,000), and carboxymethyl dextran (manufactured by Meito Sangyo Co., Ltd., molecular weight: 1,000,000), respectively. The values of Ia, Ian, S/N ratio, and the increase rate of S/N ratio are presented in Table 2.

TABLE 1

|   | Additive substance (concentration) | Ian | Ia | S/N ratio |
|---|---|---|---|---|
| Example 1 | CMD, molecular weight 500,000 (2.5 mg/mL) | 376 | 829 | 2.20 |
| Example 2 | CMD, molecular weight 500,000 (5 mg/mL) | 390 | 869 | 2.23 |
| Example 3 | CMD, molecular weight 500,000 (10 mg/mL) | 490 | 1015 | 2.07 |
| Example 4 | CMD, molecular weight 500,000 (30 mg/mL) | 872 | 1569 | 1.80 |
| Comparative Example 1 | — | 413 | 592 | 1.43 |
| Comparative Example 2 | PEG (1%) | 557 | 999 | 1.79 |
| Comparative Example 3 | PEG (3%) | 874 | 1308 | 1.50 |
| Comparative Example 4 | PEG (5%) | 1214 | 1523 | 1.25 |

TABLE 2

|   | Additive substance (concentration) | Ian | Ia | S/N ratio | Increase rate of S/N ratio (%) |
|---|---|---|---|---|---|
| Comparative Example 1 | — | 413 | 592 | 1.43 | — |
| Example 5 | CMD, molecular weight 10,000 (5 mg/mL) | 370 | 569 | 1.54 | 7% |
| Example 6 | CMD, molecular weight 40,000 (5 mg/mL) | 338 | 722 | 2.13 | 49% |
| Example 7 | CMD, molecular weight 200,000 (5 mg/mL) | 345 | 708 | 2.05 | 43% |
| Example 8 | CMD, molecular weight 500,000 (5 mg/mL) | 403 | 795 | 1.97 | 38% |
| Example 9 | CMD, molecular weight 1,000,000 (5 mg/mL) | 326 | 760 | 2.33 | 63% |

The invention claimed is:

1. A method for detecting an analyte, the method comprising:
    supplying a specimen to a detection device having a first ligand, the first ligand being immobilized on a substrate and capable of specifically binding to the analyte, the specimen being supplied onto the substrate of the detection device, and then causing the analyte included in the specimen to bind to the first ligand, wherein the substrate comprises a hydrophilic polymer layer, and the first ligand is directly immobilized to the hydrophilic polymer layer, and the speciment has been diluted with a solvent consisting of phosphate buffered saline, Tris buffered saline, or HEPES buffered saline;
    supplying a second ligand onto the substrate, the second ligand being labeled with a marker and capable of specifically binding to the analyte, and then causing the second ligand to bind to the analyte bound to the first ligand; and
    measuring the second ligand bound to the analyte,
    wherein in the supplying the second ligand, carboxymethyl dextran is supplied onto the substrate, and
    wherein the hydrophilic polymer layer is composed of carboxymethyl dextran.

2. The method for detecting an analyte according to claim 1, wherein in the supplying the second ligand, carboxymethyl dextran is supplied onto the substrate at a concentration of 1 to 30 mg/mL.

3. The method for detecting an analyte according to claim 1, wherein in the supplying the second ligand, carboxymethyl dextran is supplied onto the substrate together with the second ligand.

4. The method for detecting an analyte according to claim 3, wherein in the supplying the second ligand, a second ligand-containing liquid containing the second ligand and carboxymethyl dextran is supplied onto the substrate.

5. The method for detecting an analyte according to claim 1, wherein in the supplying the second ligand, the second ligand is supplied onto the substrate so as to cause the second ligand to bind to the analyte, and then carboxymethyl dextran is supplied thereonto.

6. The method for detecting an analyte according to claim 5, wherein in the supplying the second ligand, after the second ligand is caused to bind to the analyte, carboxymethyl dextran is supplied in the form of being incorporated into a cleaning liquid for cleaning the substrate.

7. The method for detecting an analyte according to claim 1, wherein the analyte is cardiac troponin I (cTnI) or brain natriuretic peptide (BNP).

8. The method for detecting an analyte according to claim 2, wherein in the supplying the second ligand, carboxymethyl dextran is supplied onto the substrate together with the second ligand.

9. The method for detecting an analyte according to claim 2, wherein in the supplying the second ligand, the second ligand is supplied onto the substrate so as to cause the second ligand to bind to the analyte, and then carboxymethyl dextran is supplied thereonto.

10. The method for detecting an analyte according to claim 2, wherein the analyte is cardiac troponin I (cTnI) or brain natriuretic peptide (BNP).

11. The method for detecting an analyte according to claim 3, wherein the analyte is cardiac troponin I (cTnI) or brain natriuretic peptide (BNP).

12. The method for detecting an analyte according to claim 4, wherein the analyte is cardiac troponin I (cTnI) or brain natriuretic peptide (BNP).

13. The method for detecting an analyte according to claim 5, wherein the analyte is cardiac troponin I (cTnI) or brain natriuretic peptide (BNP).

14. The method for detecting an analyte according to claim 6, wherein the analyte is cardiac troponin I (cTnI) or brain natriuretic peptide (BNP).

\* \* \* \* \*